US00PP34315P2

(12) United States Plant Patent
Hansen

(10) Patent No.: US PP34,315 P2
(45) Date of Patent: Jun. 7, 2022

(54) ***SEDUM* PLANT NAMED 'ROSY CHEEKS'**

(50) Latin Name: *Sedum hybrid*
Varietal Denomination: Rosy Cheeks

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 17/803,078

(22) Filed: Feb. 1, 2022

(51) Int. Cl.
*A01H 5/02* (2018.01)
*A01H 6/32* (2018.01)

(52) U.S. Cl.
USPC ..... Plt./479

(58) Field of Classification Search
USPC ..... Plt./479
See application file for complete search history.

*Primary Examiner* — Susan McCormick Ewoldt

(57) ABSTRACT

A new and distinct ornamental perennial *Sedum* plant named 'Rosy Cheeks' is characterized by tight-forming, compact, domed clumps with small-sized, blue-green glaucous foliage that becomes wine-colored with high light. The numerous vertical to arching branched flower stems resist falling over and opening up in the center of the plant throughout the growing season. Numerous stems produce a multitude of flowers of bright rosy-pink effect completely covering the top of the plant. The new plant is useful for the landscape in containers, as specimens, en masse.

1 Drawing Sheet

Botanical designation: *Sedum* hybrid.
Cultivar denomination: 'Rosy Cheeks'.

STATEMENT REGARDING PRIOR DISCLOSURES UNDER 37 CFR 1.77(B)(6)

The first non-enabling disclosure of the claimed plant was the photograph and brief description on a website operated by Walters Gardens, Inc. on Feb. 1, 2021. Subsequently the claimed plant was advertised in the "Walters Gardens 2021-2022 Catalog" distributed beginning May 21, 2021. The claimed plant was first privately sold on Apr. 5, 2021 by Walters Gardens, Inc., who obtained the plant and all information relating thereto, from the inventor. No plants of *Sedum* 'Rosy Cheeks' have been sold in this country or anywhere in the world, nor has any disclosure of the new plant been made, more than one year prior to the filing date of this application, and such sale or disclosure within one year was either derived directly or indirectly from the inventor and would be considered a U.S.C. § 102(b) exception.

BACKGROUND OF THE INVENTION

The present invention relates to a new and distinct cultivar of *Sedum* plant, botanically known as *Sedum* and hereinafter referred to by the cultivar name 'Rosy Cheeks'. There are over 300 recognized species of the genus *Sedum*.

The new *Sedum* plant is a selection of a planned breeding program conducted by the inventor, at a wholesale perennial nursery in Zeeland, Mich., USA.

The new *Sedum* plant was selected as a single seedling from an insect pollinated cross in an isolation block Aug. 7, 2013 between an unnamed selection of *Sedum tatarinowii* (not patented) as the female or pod parent and a proprietary unreleased selection of *Sedum cauticola* (not patented) as the male or pollen parent. *Sedum* 'Rosy Cheeks' was assigned the breeder code number 13-40-102 to keep it separated from among thousands of other seedlings of this and other crosses when it progressed through the initial trial phase in the fall of 2015. The selected single seedling clone was originally selected for it strong, healthy, dense growth, colorful foliage and flowers and intermediate traits between the two parents.

Asexual reproduction of *Sedum* 'Rosy Cheeks' by division at a wholesale perennial nursery in Zeeland, Mich., USA since September of 2015 and subsequent vegetative shoot tip cuttings has shown that the unique features of this new *Sedum* plant are stable and reproduced true to type in successive generations.

SUMMARY OF THE INVENTION

Plants of *Sedum* 'Rosy Cheeks' have not been observed under all possible environmental conditions. The phenotype may vary somewhat with variations in environment such as temperature, available water, fertility and light intensity without, however, any variation in genotype.

The following traits have been repeatedly observed and are determined to comprise the unique characteristics of *Sedum* 'Rosy Cheeks' and distinguish it as a new and distinct autumn stonecrop plant unique from all other autumn stonecrop plants known to the inventor:

1. Tight-forming compact domes with vertical to arching stems;
2. Center stems remain erect throughout the growing season produce full habit;
3. Small-sized, blue-green, glaucous foliage that becomes wine-colored with high light;
4. Numerous, branched, blue-green to wine-colored stems produce flower clusters of bright rosy-pink completely cover the top of the plant.

In comparison with the female parent, the new plant has a larger width and height and retains its upright stems better through the entire growing season. The nearest comparison varieties known to the inventor are: 'Crystal Pink' U.S. Plant Pat. No. 22,094, 'Pillow Talk' U.S. Plant Pat. No. 28,528, 'Powder Puff' U.S. Plant Pat. No. 32,714, 'Pride and Joy' U.S. Plant Pat. No. 32,530 and 'Pure Joy' U.S. Plant Pat. No. 24,194.

Compared with 'Crystal Pink', the new plant is shorter in flower with more flower coverage of a deeper rosy-pink flower, and has smaller leaves that become wine-colored. 'Pillow Talk' has larger habit and leaves, less stem strength at flowering with flowers that are magenta-colored. 'Powder Puff' has flowers that are a deeper rosy-pink and the foliage becomes wine-colored. 'Pride and Joy' has slightly taller habit and the flowers are purplish-pink on darker flower stems, and the foliage is more grey-green with smaller marginal teeth. 'Pure Joy' has lighter pink bicolor flowers and lacks the wine-colored foliage.

The female parent has thinner stems, smaller foliage with larger marginal teeth, and the flower is near white. The male parent has a smaller habit foliage that is not serrate, and the with flowers are lighter colored and begin later in the season.

BRIEF DESCRIPTION OF THE PHOTOGRAPHS

The photograph of the new plant demonstrates the unique traits and the overall appearance of *Sedum* 'Rosy Cheeks'. The colors are as accurate as reasonably possible with color reproductions of this type. Variations in ambient light spectrum, source and direction may cause the appearance of minor variation in color. The plants used in the photograph were grown in an open, full-sun trial garden at a wholesale perennial nursery in Zeeland, Mich. with supplemental water and fertilizer when needed. No plant growth regulators or pinching have been used.

DETAILED BOTANICAL DESCRIPTION

Figure 1:
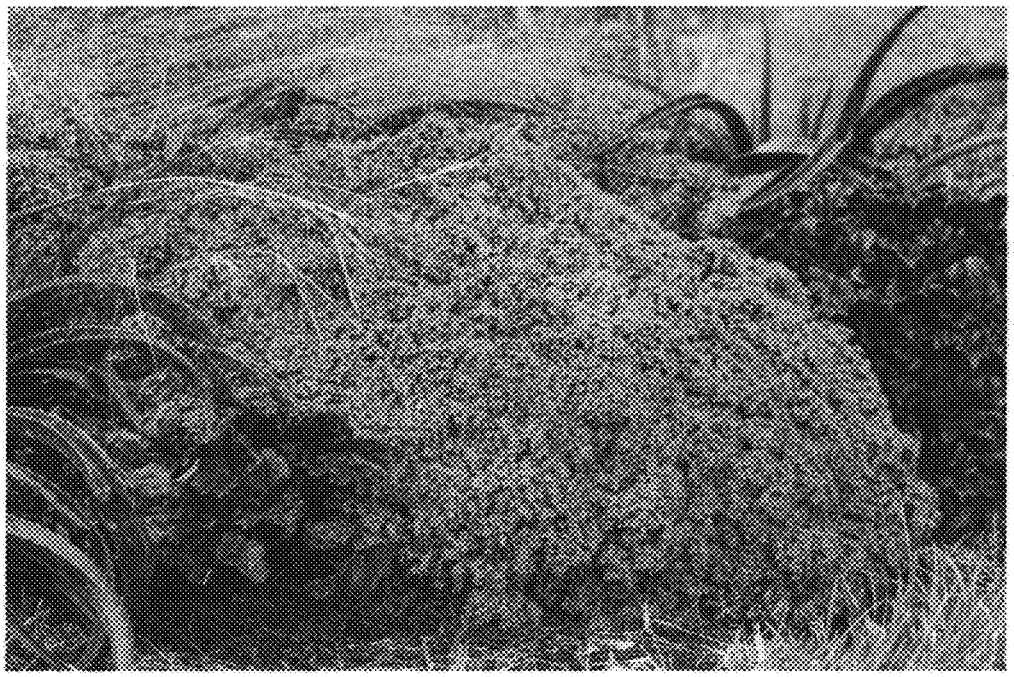
FIG. 1 shows a four-year-old plant in early stages of flowering with extensive flower coverage.
Figure 2:
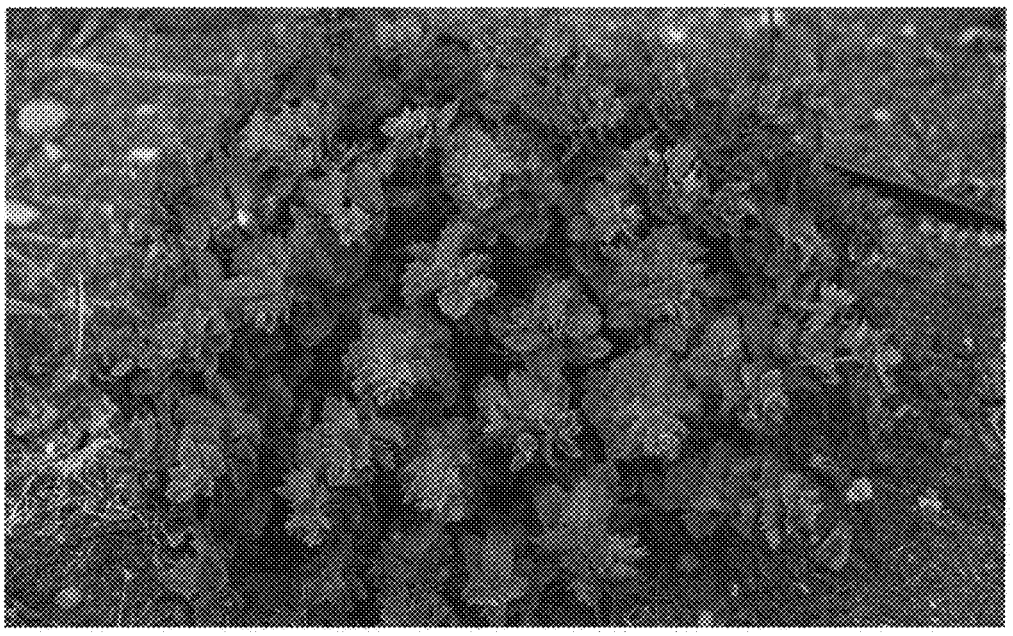
FIG. 2 shows the variable color of the foliage of a two-year-old plant in mid-summer prior to flowering.

The following is a detailed description of four-year-old plants of the new cultivar as grown outdoors in a full sun trial plot at a wholesale nursery in Zeeland, Mich. No plant growth regulators have been used. Plants of the new cultivar have not been tested under all possible conditions. The phenotype may vary with changes in environment, climate, and cultural conditions without change however in the genotype. The color reference is in accordance with the 2015 edition of The Royal Horticultural Society Colour Chart except where general color dictionary terms are used.

Botanical designation: *Sedum* hybrid;

Cultivar denomination: 'Rosy Cheeks';

Parentage: A selection of *Sedum tatarinowii* plant as the female or seed parent; a proprietary unreleased selection of *Sedum cauticola* as the male or pollen parent;

Asexual propagation: Stem tip cuttings and division;

Time to initiate roots: About two weeks;

Time to finish a 3.8 liter flowering container: About three months in the summer from a rooted 2.5 cm plug;

Root description: Thick, fleshy; freely branching; creamy white to light tan in color.

Plant habit: Winter-hardy herbaceous perennial; clumping mound; stems stiff and upright to arching arising from a dense crown; dense and full, not opening in center later in the season; flower heads freely branching;

Growth rate: Moderately vigorous;

Plant size: About 27.0 cm tall and 75.0 cm wide in full flower;

Stems: Terete; glaucous; glabrous; to about 7.0 mm diameter at the base and about 35.0 cm long from base to initial branches; 32 internodes per stem below inflorescence, average length about 9.0 mm; about 80 stems per plant;

Stem color: Variable, proximally and where protected from high light exposure between RHS 146D and RHS 147D, with increased light exposure nearest RHS 187A;

Lateral branches: Glaucous; primary branches to about 9.0 cm long and about 3.0 mm diameter; moderately to heavily branched with 5 main branches;

Lateral branch color: Proximally between RHS 147C and RHS 146C, with increasing blushing distally to nearest RHS 187B;

Foliage: Ovate; alternate to sub-opposite; simple; smooth; glabrous and glaucous on both surfaces; sessile; thick, sarcous and succulent; apex bluntly acute to rounded; base attenuate; margin irregularly and moderately dentate, about 5 teeth in distal two-thirds of leaf; teeth about 2.0 mm long, and 4.0 mm apart; attitude outward;

Foliage size: To about 3.5 cm long, 2.4 cm across and 3.0 mm thick; average about 2.8 cm long, 1.7 cm across and 2.0 mm thick;

Foliage color: Adaxial young between RHS N138B and RHS 147C, abaxial young between RHS 138B and RHS 147C; mature adaxial between RHS N186B and RHS 187B and abaxial nearest RHS N138C;

Petiole: Leaves sessile;

Venation: Palmate, barely distinguishable; midrib slightly raised abaxial;

Vein color: Abaxial and adaxial secondary veins same as surrounding leaf tissue; adaxial midrib nearest RHS 138B, abaxial midrib nearest RHS 148D and;

Flower: Stellate, actinomophic; pentamerous; persistent; attitude upright to outwardly in terminal compound cymes; size about 7.0 mm across and 4.0 mm deep;

Flower number: About 800 per stem and 10,000 to 20,000 flowers per plant;

Fragrance: None detected;

Flowering season: Beginning mid to late August in Zeeland, Mich. for about four weeks;

Longevity: Flower cymes remain effective for about three weeks on the plant and one week as cut flowers; individual flowers and calyces persistent and effective for about three weeks;

Flower buds about one day prior to opening: Ovoid; apex acute; base rounded; about 4.0 mm long and about 2.5 mm diameter near middle;

Flower bud color: Nearest RHS 194D proximally and between RHS 71A and RHS N77B distally;

Inflorescence: About 9.0 cm tall from first branch and about 10.0 cm across; up to about 800 flowers per branched inflorescence;

Petals: Five; lanceolate; acute apex; base fused; margin entire; glabrous and lustrous abaxial and adaxial; average about 4.0 mm long and about 1.5 mm across near middle;

Petal color: When initially open adaxial between RHS 64B and RHS 64C, distally nearest RHS 64A; when initially open abaxial distally nearest RHS 186C proximally and distally nearest RHS 64A; when mature adaxial nearest RHS 186A distally and RHS 186D proximally; when mature abaxial between RHS N186C and RHS N186B along center and edges nearest RHS 186C;

Calyx: With five sepals; campanulate; about 2.5 mm across and 1.5 mm deep;

Sepals: Linear to lanceolate; narrowly acute apex; fused in basal 0.5 mm; entire margin; glabrous and slightly glaucous both abaxial and adaxial; adpressed to petals, about 2.0 mm long and about 1.0 mm across at fusion;

Sepal color: Abaxial and adaxial nearest 148B with moderate blush of nearest RHS 187A;

Peduncles: Terete; slightly glaucous, glabrous; stiff and flexible; freely branching; upright to slightly outwardly; with branches to about 45° from perpendicular; about 9.0 cm long and 5.0 mm diameter;

Peduncle color: Nearest RHS 187A;

Pedicels: Cylindrical; glabrous, slightly glaucous; strong and stiff, yet flexible; about 2.0 mm long and 0.5 mm diameter;

Pedicel color: Nearest RHS 187B;

Androecium: Typically ten stamens;

*Filaments*.—Cylindrical; outwardly; alternately free between petals, and fused to inner corolla in basal 1.0 mm; about 3.5 mm long and about 0.2 mm diameter; color nearest RHS 64B.

*Anthers*.—Basifixed; globose; about 0.5 mm diameter; color nearest RHS N77A.

*Pollen*.—Moderate in quantity; color nearest RHS NN155A.

Gynoecium: Typically five; cylindrical, conic in distal one third; about 3.0 mm long;

*Style*.—Terete; ellipsoidal, tapering distally and base truncate; about 1.0 mm long and 0.5 mm diameter at point of attachment to ovary; glabrous; color nearest RHS NN74B.

*Stigma*.—Minute, acute; about 0.1 mm diameter and 0.1 mm long; color nearest RHS 71A.

*Ovary*.—Nearly terete, acutely tapering at apex to style; base truncate; lustrous; about 2.0 mm long and 1.0 mm diameter; color initially nearest RHS 64B, maturing to nearest RHS 148D after petals dry.

Fruit: Ventrally dehiscent follicle; about 2.2 mm long and 2.0 mm across; color at maturity nearest RHS 177A;

Seed: Sparse; fine; lanceolate; about 1.0 mm long and less than 0.2 mm across; color between RHS 165A and RHS 165B;

Growing conditions: Plants of the new *Sedum* 'Rosy Cheeks' is xeromorphic and grow best with good drainage, full sun and moderate to low fertility. 'Rosy Cheeks' is cold hardy from USDA zones 3 to 9 and has tolerated temperatures of at least 35 degrees C. 'Rosy Cheeks' tolerates heavy rains and wind and is not prone to develop an open center later in the season as many other *Sedum* cultivars do.

Disease and pest resistance: Other pest and disease resistance and tolerance outside that normal for *Sedum* is not known.

It is claimed:

1. A new and distinct perennial *Sedum* plant named 'Rosy Cheeks' as herein described and illustrated.

* * * * *